United States Patent
Stouffer et al.

(10) Patent No.: US 9,498,632 B2
(45) Date of Patent: Nov. 22, 2016

(54) RECEIVER AND DIGITAL DEMODULATION CIRCUITRY FOR AN EXTERNAL CONTROLLER USEABLE IN AN IMPLANTABLE MEDICAL DEVICE SYSTEM

(71) Applicant: Boston Scientific Neuromodulation Corporation, Valencia, CA (US)

(72) Inventors: Thomas W. Stouffer, Chatsworth, CA (US); Daniel Aghassian, Glendale, CA (US); Lev Freidin, Simi Valley, CA (US); Vasily Dronov, San Jose, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 169 days.

(21) Appl. No.: 13/942,073

(22) Filed: Jul. 15, 2013

(65) Prior Publication Data
US 2014/0022092 A1   Jan. 23, 2014

Related U.S. Application Data

(60) Provisional application No. 61/673,836, filed on Jul. 20, 2012.

(51) Int. Cl.
| | |
|---|---|
| G08C 19/22 | (2006.01) |
| H04Q 9/00 | (2006.01) |
| G08B 23/00 | (2006.01) |
| G08C 15/06 | (2006.01) |
| A61N 1/372 | (2006.01) |
| H04L 27/156 | (2006.01) |
| H04L 27/06 | (2006.01) |

(52) U.S. Cl.
CPC ......... *A61N 1/37217* (2013.01); *A61N 1/3727* (2013.01); *A61N 1/37235* (2013.01); *H04L 27/1566* (2013.01); *H04L 27/06* (2013.01)

(58) Field of Classification Search
USPC ........... 340/870.02, 870.01, 870.07; 128/903
See application file for complete search history.

(56) References Cited

U.S. PATENT DOCUMENTS

| | | | |
|---|---|---|---|
| 5,022,404 A | 6/1991 | Hafner | |
| 5,757,862 A * | 5/1998 | Ishizu | H04L 27/2331 329/304 |

(Continued)

OTHER PUBLICATIONS

Su, Kendall L, Fundamentals of Circuit Analysis, 1993, Chapter 8, Analysis of AC Circuits, pp. 378-379.*

(Continued)

*Primary Examiner* — Firmin Backer
*Assistant Examiner* — Jerold Murphy
(74) *Attorney, Agent, or Firm* — Lewis, Reese & Nesmith, PLLC

(57) ABSTRACT

Receiver and digital demodulation circuitry for an external controller for communicating with an implantable medical device (IMD) is disclosed. A Digital Signal Processor (DSP) is used to sample received analog data transmitted from the IMD at a lower rate than would otherwise be required for the frequency components in the transmitted data by the Nyquist sampling criteria. To allow for this reduced sampling rate, the incoming data is shifted to a lower intermediate frequency using a switching circuit. The switching circuit receives a clock signal, which is preferably but not necessarily the same clock signal used by the DSP to sample the data. The switching circuit multiplies the received data with the clock signal to produce lower intermediate frequencies, which can then be adequately sampled at the DSP at the reduced sampling rate per the Nyquist sampling criteria.

39 Claims, 6 Drawing Sheets

(56) References Cited

U.S. PATENT DOCUMENTS

| | | | |
|---|---|---|---|
| 5,843,139 A | 12/1998 | Goedeke et al. | |
| 8,081,952 B2 | 12/2011 | Thornton et al. | |
| 2007/0053466 A1* | 3/2007 | Klostermann | H04L 27/2331 375/316 |
| 2007/0260293 A1* | 11/2007 | Carpenter | A61N 1/3727 607/60 |
| 2009/0069869 A1 | 3/2009 | Stouffer et al. | |

OTHER PUBLICATIONS

U.S. Appl. No. 13/900,877, filed May 23, 2013, Stouffer et al.
International Search Report and Written Opinion regarding PCT Application No. PCT/US2013/051067, dated Nov. 4, 2013.

* cited by examiner

RECEIVER AND DIGITAL DEMODULATION CIRCUITRY FOR AN EXTERNAL CONTROLLER USEABLE IN AN IMPLANTABLE MEDICAL DEVICE SYSTEM

CROSS REFERENCE TO RELATED APPLICATIONS

This is a non-provisional of U.S. Provisional Patent Application Ser. No. 61/673,836, filed Jul. 20, 2012, to which priority is claimed and which is incorporated herein by reference.

FIELD OF THE INVENTION

The present invention relates to improved receiver and demodulation circuitry useable in an external controller that communicates with an implantable medical device.

BACKGROUND

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIG. 1, a SCS system typically includes an Implantable Pulse Generator (IPG) 100, which includes a biocompatible device case 30 formed of titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102 and 104 couple to the IPG 100 using lead connectors 38a and 38b, which are fixed in a header material 36, which can comprise an epoxy for example. In a SCS application, electrode leads 102 and 104 are typically implanted on the right and left side of the dura within the patient's spinal cord. These leads 102 and 104 are then tunneled through the patient's flesh to a distant location, such as the buttocks, where the IPG 100 is implanted.

FIG. 2A shows a plan view of an external controller 12 used to wirelessly communicate with the IPG 100, while FIG. 2B shows a cross section of the external controller 12 and the IPG 100. As shown in FIG. 2B, the IPG 100 typically includes an electronic substrate assembly 14 including a printed circuit board (PCB) 16, along with various electronic components 20, such as a microcontroller, integrated circuits, and capacitors mounted to the PCB 16. Two coils are generally present in the IPG 100: a telemetry coil 13 used to transmit/receive data to/from the external controller 12; and a charging coil 18 for charging or recharging the IPG's battery 26 using an external charger (not shown). The telemetry coil 13 can be mounted within the header 36 of the IPG 100 as shown, but can also be provided within the case 30, as disclosed in U.S. Patent Publication 2011/0112610 for example.

The external controller 12, such as a patient hand-held programmer or a clinician's programmer, is used to send data to and receive data from the IPG 100. For example, the external controller 12 can send programming data such as therapy settings to the IPG 100 to dictate the therapy the IPG 100 will provide to the patient. Also, the external controller 12 can act as a receiver of data from the IPG 100, such as various data reporting on the IPG's status. As shown in FIG. 2B, the external controller 12, like the IPG 100, also contains a PCB 70 on which electronic components 72 are placed to control operation of the external controller 12. The external controller 12 is powered by a battery 76, but could also be powered by plugging it into a wall outlet for example.

The external controller 12 typically comprises a graphical user interface 74 similar to that used for a portable computer, cell phone, or other hand held electronic device. The graphical user interface 74 typically comprises touchable buttons 80 and a display 82, which allows the patient or clinician to operate the external controller 12 to update the therapy the IPG 100 provides, and to review any relevant status information that has been reported from the IPG 100.

Wireless data transfer between the IPG 100 and the external controller 12 preferably takes place via inductive coupling between a telemetry coil 73 (FIG. 2B) in the external controller 12 and the telemetry coil 13 in the IPG 100. Either coil 13 or 73 can act as the transmitter or the receiver, thus allowing for two-way communication between the two devices. Typically, the transmitting device will send data to the receiving device via a Frequency Shift Keying (FSK) protocol in which different data states are indicated by different frequencies. For example, a transmitting device may send a logic '0' bit to the receiving device at 121 kHz, but may send a logic '1' bit at 129 kHz. That is, the data is represented relative to a center frequency $f_c$=125 kHz, with the logic states representing a +/−4 kHz deviation from this center frequency. Bits may be serially transferred in this fashion at a given rate of 4 k bits/sec (4 kHz), i.e., a bit duration of $t_b$=250 µs for example, meaning that a logic '0' bit roughly comprises 30 cycles at 121 kHz (121/4), while a logic '1' bit roughly comprises 32 cycles at 129 kHz (129/4). These frequencies are not significantly attenuated in the patient's tissue 25, and so data transmission can occur transcutaneously using this scheme.

FIG. 3 illustrates prior art receiver and demodulation circuitry 150 used in an external controller 12 to receive and recover FSK data transmitted from the IPG 100. The circuitry 150 includes a L-C tank circuit 151 (or antenna, more generally) comprising a serial connection between the telemetry coil 73 and a tank capacitor C. (A parallel arrangement can also be used). The inductance L of the coil 73 or the capacitance of the tank capacitor C can be tuned to generally allow the tank circuit 151 to resonate at the center frequency $f_c$=125 kHz of the data expected from the IPG 100.

The low-amplitude AC signal received at coil 73 is amplified at a pre-amplifier 152, where it is them mixed with a 330 kHz reference signal at a mixer 154 to produce a signal with an intermediate frequency of $f_{c-if}$=455 kHz. This is done in the prior art because 455 kHz comprises a well-known standard communication frequency, and as a result, receiver components are readily available to operate at this frequency. See, e.g., http://en.wikipedia.org/wiki/Intermediate_frequency. Mixer 154 can be implemented using Part No. MAX 4636, manufactured by Maxim Integrated Products, Inc.

After mixing, the up-shifted frequency is provided to a band pass filter (BPF) 156, centered at $f_{c\text{-}if}$=455 kHz and with a bandwidth (BW) of 12 kHz. This BPF 156 reduces noise outside of the band of frequencies of interest (i.e., below 449 kHz and above 461 kHz), while allowing the signals from the IPG 100 ($f_{0\text{-}if}$=121 k+330 k=451 kHz, and $f_{1\text{-}if}$=129 k+330 k=459 kHz) to readily pass. Thereafter, the signals are passed to a limiting amplifier 158 which limits the magnitude of the signals by clipping their peaks if necessary, as is well known. Another BPF similar to BPF 156 can be provided after the limiting amplifier 158 to remove any out-of-band frequency components resulting from clipping, but this is not shown for simplicity. The BFP(s) can comprise ceramic filters, such as Part No. AHCFM2-455AL, manufactured by Toko America, Inc., or Part No. CFUM455D, manufactured by Murata Manufacturing Co.

Thereafter, the received signal is demodulated. This occurs first by sending the signals to a multiplier 160, which multiplies the signal with a phase-shifted version of the signal provided by phase shift block 162. The quad coil 163 in the phase shift block 162 is tunable to provide a 90-degree phase shift at $f_{c\text{-}if}$=455 kHz, but will provide different phase shifts θ for the FSK signals of interest ($f_{0\text{-}if}$=451 kHz, and $f_{1\text{-}if}$=459 kHz). The output of the multiplier comprises $\cos(2\pi f)*\cos(2\pi f+\theta)$, or $(\frac{1}{2})\cos(\theta)+(\frac{1}{2})\cos(4\pi f+\theta)$. A low pass filter (LPF 164) removes the AC component of this product ($(\frac{1}{2})\cos(4\pi f+\theta)$), and allows only the DC component ($(\frac{1}{2})\cos(\theta)$) to pass as analog signal 165. Because θ produced by the phase shift block 162 is different at $f_{0\text{-}if}$ and $f_{1\text{-}if}$, the data becomes apparent at this point, although it may be substantially noisy.

The limiting amplifier 158 and multiplier 160 can comprise portions of the same demodulator integrated circuit, such as Part No. Part No. SA608DK, manufactured by NXP Semiconductors N.V.

The analog signal 165 is provided to an Analog-to-Digital converter (A/D) block 172, which can comprise a discrete block or an A/D input of a microcontroller 170 of the external controller 12 as shown. The signal 165 is sampled at an appropriate rate, and the resulting digitized values of the amplitude of the signal 165 at different points in time are stored in memory 174. Once stored, a digital filter 176, operating as software in the microcontroller 170, can operate on the stored data to remove noise and recover the data as a digital bit stream 177. The particulars of filter 176 are not important, and are not further discussed.

While the receiver and demodulation circuitry 150 of the prior art external controller 12 of FIG. 3 functions well, the inventors see room for improvement. First, circuitry 150 is relatively expensive, as it uses relatively expensive components, such as the demodulator IC and the ceramic band pass filter(s). Further, circuitry 150 has reliability and manufacturing concerns. The ceramic band pass filter(s) are fragile and can break, which is of particular concern in an external controller 12 that may from time to time be dropped by the patient. The quad coil 163 in the phase shift block 162 is also difficult to work with, as it requires special handling in manufacturing, and must be tuned by hand to ensure that it provides the proper 90-degree shift at the center frequency $f_{c\text{-}if}$=455 kHz.

Given these shortcomings, the art of implantable medical devices would benefit from improved receiver and demodulation circuitry for an external controller, and this disclosure presents solutions.

DETAILED DESCRIPTION

Figure 1:
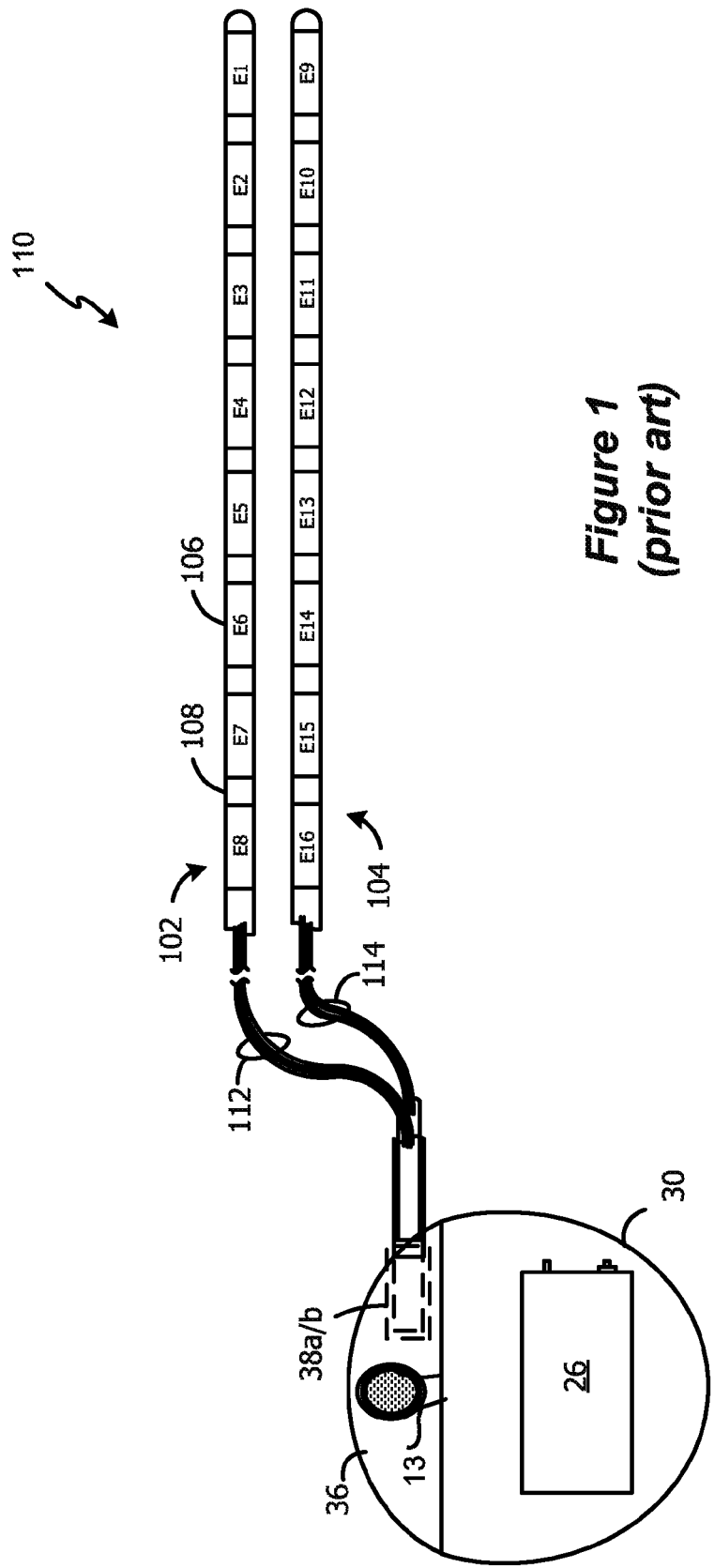
FIG. 1 shows an Implantable Pulse Generator (IPG) in accordance with the prior art.
Figure 2:
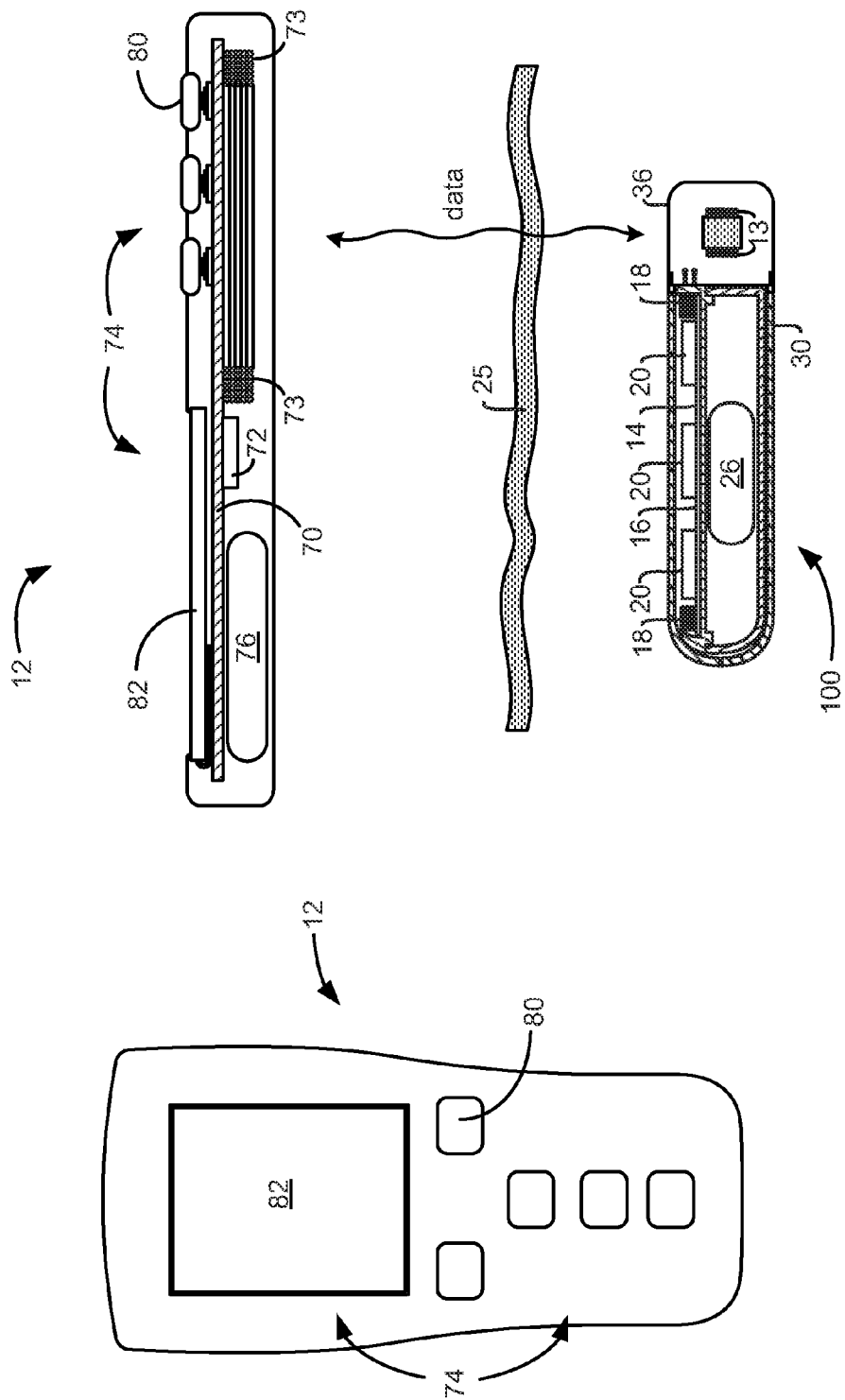
FIGS. 2A and 2B show an external controller for communicating with an IPG in accordance with the prior art.

The disclosed external controller digitally demodulates data transmitted from the IPG 100. Digital demodulation can be performed using a Digital Signal Processor (DSP) integrated circuit, and many DSPs have analog-to-digital (A/D) converters that can digitize the received analog signals, so that they can thereafter be digitally filtered and processed to demodulate the received data. DSPs however can be expensive, which is undesired as this raises the cost of the external controller. Generally speaking, the cost of a DSP having analog inputs scales with the speed at which the DSP is able to sample the analog data: that is, DSPs with high sampling rates tend to be more expensive. By contrast, less expensive DSPs with lower sampling rates may not be acceptable to sample the data transmitted from the IPG. To resolve the transmitted FSK data without aliasing, a DSP used in an external controller would generally have to sample at a frequency of at least 258 kHz, i.e., twice the highest FSK frequency of interest ($f_1$=129 kHz) in accordance with the well-known Nyquist sampling criteria. DSPs capable of sampling at this rate are in the inventors' opinion too expensive, and would inflate the cost of the external controller.

To address this concern, the inventors' disclosed approach uses a DSP that samples at a lower rate than would otherwise generally be required to sample the FSK data. For example, in the disclosed solution, the DSP samples the data at 192 kHz—less than the 258 kHz specified by the Nyquist sampling criteria for the FSK data at issue. To allow this reduced sampling rate to be effective from a Nyquist sampling perspective, the incoming FSK data is shifted to a lower intermediate frequency, for example $f_{0\text{-}if}$=71 kHz and $f_{1\text{-}if}$=63 kHz. Because 192 kHz is well above twice this highest frequency (i.e., above 2 times 71 kHz=142 kHz), the data can be sampled and demodulated by the DSP without fear of aliasing.

The incoming FSK data is shifted to the lower intermediate frequency using a switching circuit. The switching circuit receives a clock signal from the DSP, which is preferably the same 192 kHz clock signal that is used by the DSP to sample the data. By porting this clock signal outside of the DSP to the switching circuit, the switching circuit in effect multiplies the received FSK data with the clock signal to produce higher and lower intermediate frequencies. The resulting intermediate frequency signals are then sampled at the A/D input of the DSP using the 192 kHz clock signal. Sampling at this rate is suitable from a Nyquist sampling perspective for the lower intermediate frequencies (e.g., $f_{0\text{-}if}$=63 kHz and $f_{1\text{-}if}$=71 kHz), which allows the DSP to then reliably filter and demodulate the received signal. Higher frequency components—which may be of too high a frequency to be adequately sampled using the 192 kHz clock signal per the Nyquist sampling criteria—are essentially ignored or filtered out.

Thus, and as will be seen, the inventors' solution uses a relatively low speed, low cost DSP integrated circuit, and the improved receiver and demodulation circuitry provides a robust solution involving few components, and which is easier and cheaper to manufacture. For example, hand-tunable quad coils and delicate ceramic band pass filters are not required.

Figure 4:
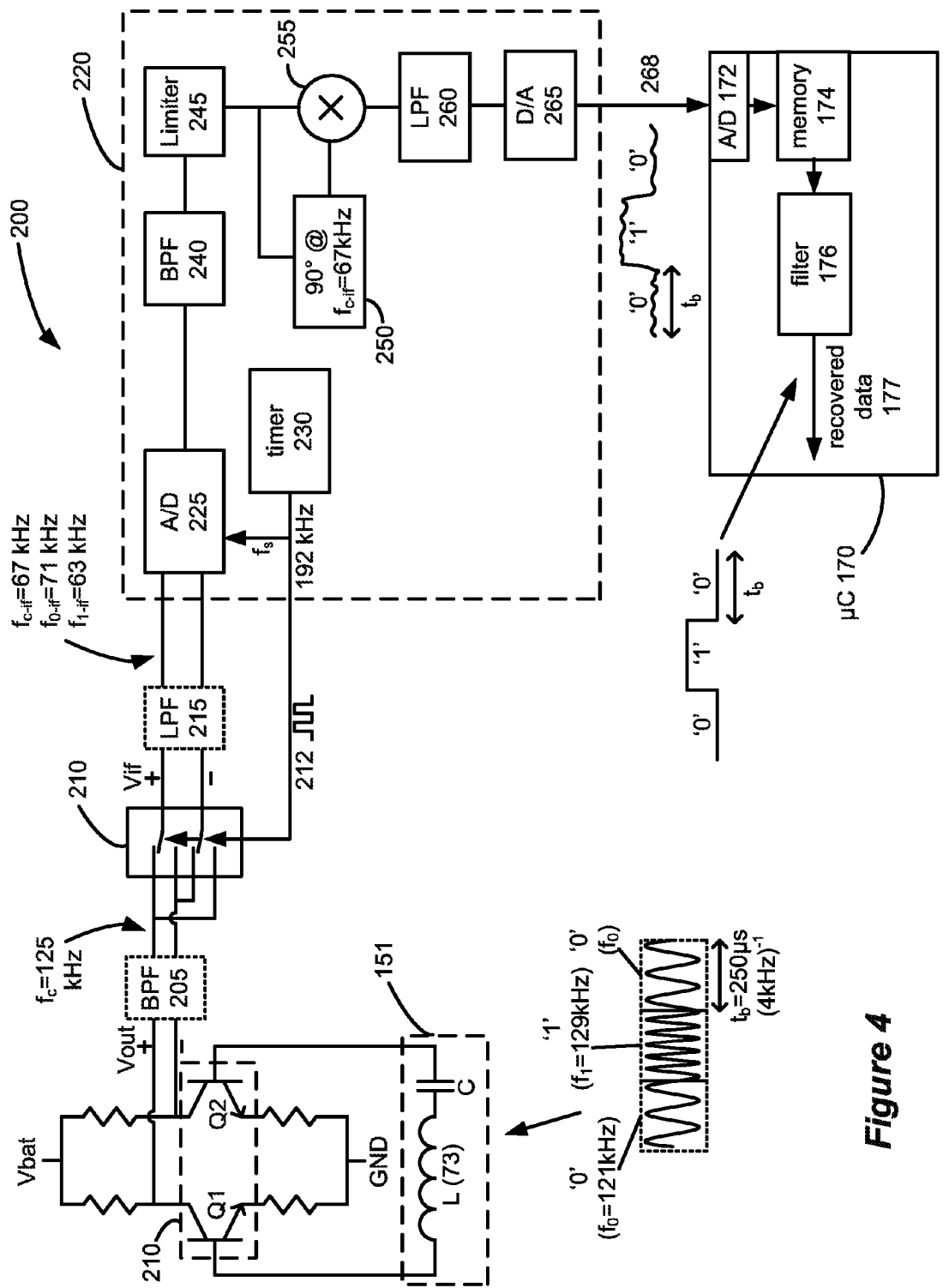
FIG. 4 shows improved receiver and demodulation circuitry useable in an external controller in accordance with an embodiment of the invention.

FIG. 4 shows an embodiment of improved receiver and demodulation circuitry 200 for an external controller 12, which includes a DSP 220 and front-end receiver circuitry. The DSP 220, in one example, comprises Part No. ADAU1701, manufactured by Analog Devices, Inc. The data sheet for this component is attached hereto, and is incorporated herein by reference in its entirety. This DSP 220 happens to be marketed as an audio processor, but has nonetheless been determined by the inventors to be suitable for the telemetry application at hand. However, using this particular DSP 220 is not strictly required, and other DSPs could be used instead.

The improved circuitry 200, like the prior art circuitry 150 described earlier, comprises a tank circuit 151 with a telemetry coil 73 and a tank capacitor C, which can be connected in series as shown or in parallel (not shown). As before, the values for these components are chosen to generally resonate at the center frequency $f_c$=125 kHz of the FSK data expected from the IPG 100.

The small AC signal from the coil 73 is provided to a differential amplifier 202, formed using bipolar transistors Q1 and Q2. Each transistor receives opposing signals from the tank circuitry 151 at their bases and provides an output at their collectors, which outputs together provide a single differential output, Vout. The particulars of amplifier 202 are not important, and amplifier 202 could be made in other ways, although the disclosed circuit is preferred because of its simplicity, reliability, and the low cost of its components. Other types of amplifier circuits could also be used. At this point, Vout can be sent to a band pass filter (BPF) 205 if desired to screen out-of-band frequencies (i.e., frequencies below 121 kHz and above 129 kHz). However, use of a BPF 205 is not necessary, and so it is shown in dotted lines.

Vout, whether filtered or not, is sent to a switching circuit 210, which in one example may comprise Part No. FSA2588, manufactured by Fairchild Semiconductor Corp. As shown, the switching circuit 210 comprises two switches, each controlled by a clock signal 212 issued by a timer 230 in the DSP 220. Switching circuit 210 effectively comprises a type of multiplier, as will be discussed below. Clock signal 212 comprises in this example a 192 kHz square wave signal. As discussed in the above-incorporated data sheet for Part No. ADAU1701, the clock signal 212 can be formed as signal LRCLK, and output to pin MP10 (OUTPUT_LR-CLK). OLF is set to '0' in the Serial Out Register for OUTPUT_LRCLK to be the same frequency as the sampling frequency, $f_s$, and $f_s$ is set to 192 kHz in the SR bits of the DSP core register.

Differential signal Vout is flipped at the input to the two switches, with the effect that Vout is inverted at the output of the switches (Vif) when clock signal 212 changes state. This operates to shift Vout to intermediate frequencies, Vif. Mathematically, and representing Vout at a center frequency for the FSK data of interest ($f_c$=125 kHz), Vif can be understood as multiplying Vout=cos(2π*125 k*t) by clock signal 212=sgn(cos(2π*192 k*t)), where "sgn" comprises the sign (either 1 or −1) of its argument. Multiplying these two functions yields the result:

$$Vif = \cos(2\pi*125k*t)*\text{sgn}(\cos(2\pi*192k*t))$$

$$= \frac{[\cos(2\pi*125k*t)*\cos(2\pi*192k*t)]}{|\cos(2\pi*192k*t)|}$$

$$= \frac{1/2[\cos(2\pi*(192k-125k)*t)+\cos(2\pi*(192k+125k)*t)]}{|\cos(2\pi*192k*t)|}$$

$$= \frac{1/2[\cos(2\pi*67k*t)+\cos(2\pi*317k*t)]}{|\cos(2\pi*192k*t)|}$$

Thus, Vif is comprised of two intermediate center frequencies, 67 kHz and 317 kHz, as well as the frequency 192 kHz of the switching signal 212. The FSK data of interest ranges around the two center frequencies, with $f_{0\text{-}if}$ equaling either 71 kHz (i.e., 192 k−121 kHz) or 313 kHz (192 kHz+121 kHz), and $f_{1\text{-}if}$ equaling either 63 kHz (i.e., 192 k−129 kHz) or 321 kHz (192 kHz+129 kHz). Because a goal of improved circuitry 200 is to reduce the frequency of the incoming signal ($f_c$=125 kHz) to ease rate at which the signal must be digitally sampled by the DSP 220, only the lower FSK components of interest, $f_{0\text{-}if}$=71 kHz and $f_{1\text{-}if}$=63 kHz, are ultimately demodulated to recover the data transmitted by the IPG 100. An optional low pass filter (LPF) 215 can be used to pass these lower FSK components of interest, and to reject the higher components (192 kHz and those centered around 317 kHz) in Vif, but this is not strictly necessary, as such higher-frequency components will be filtered out and ignored once processed in the DSP 220.

Whether filtered or not, the FSK signals of interest, $f_{0\text{-}if}$=71 kHz and $f_{1\text{-}if}$=63 kHz, are input to an A/D block 225 in the DSP 220 for sampling and processing. (If Part No. ADAU1701 is used, such inputs comprise ADC0 and ADC1). Timer 230 in the DPS issues the clock signal 212 as discussed above, which is used to sample and digitize Vif at a rate of $f_s$=192 kHz. As discussed earlier, this sampling frequency is sufficient from a Nyquist sampling perspective to sample the intermediate-frequency-shifted FSK signals of interest. Higher frequency components in Vif (such as those centered at 317 KHz and 192 kHz) will not be sampled at a fast enough rate, and will in any event be rejected by the processing to follow in the DSP 220.

Thereafter, the DSP 220 is programmed to filter and demodulate the data digitized by the A/D block 225. Such processing can involve many of the same steps discussed earlier in conjunction with the prior art, albeit in digital processing form. For example, the data can be subject to a band pass filter 240, which will pass only the frequencies of interest data, i.e., a band of frequencies including $f_{0\text{-}if}$=71 kHz and $f_{1\text{-}if}$=63 kHz. A limiter 245 can be used to clip the magnitude of the signals. A multiplier 255 in conjunction with a 90° phase shift circuit (@ $f_{c\text{-}if}$=67 kHz) 250 can be used to demodulate the data. The resulting data can be subject to a low pass filter (LPF) 260 to remove DC components and produce digital demodulated samples.

Figure 3:
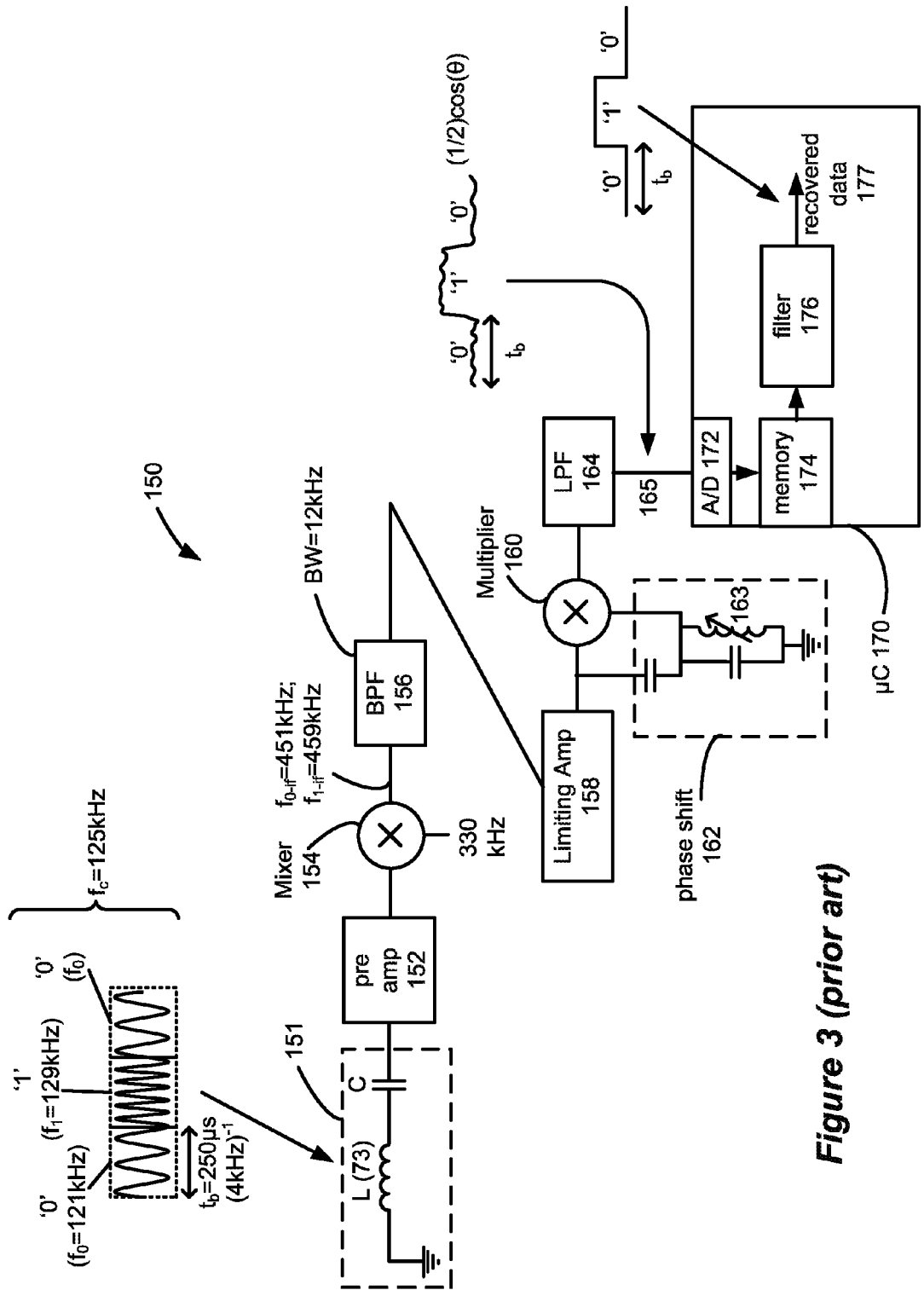
FIG. 3 shows receiver and demodulation circuitry useable in the external controller of the prior art.

Finally, a digital-to-analog (D/A) converter 265 can be used to form an analog signal 268 comprising the demodulated digital samples (akin to analog signal 165 of the prior art, FIG. 3), which analog signal 268 can then be sent to the microcontroller 170 in the external controller 12 to be recovered as digital data 177, which may include sampling (172), storage (174), and filtering (176) (FIG. 3). Note however that it may not be strictly necessary to convert the demodulated digital samples to an analog signal 268 at D/A block 265. For example, the demodulated digital samples output by LPF 260 may be sent directly to the microcontroller in digital form or elsewhere in the external controller 12 via a digital bus and without conversion. "Demodulated digital samples" should thus be construed as including both digital and analog (268) data sent to the microcontroller.

Figure 5:
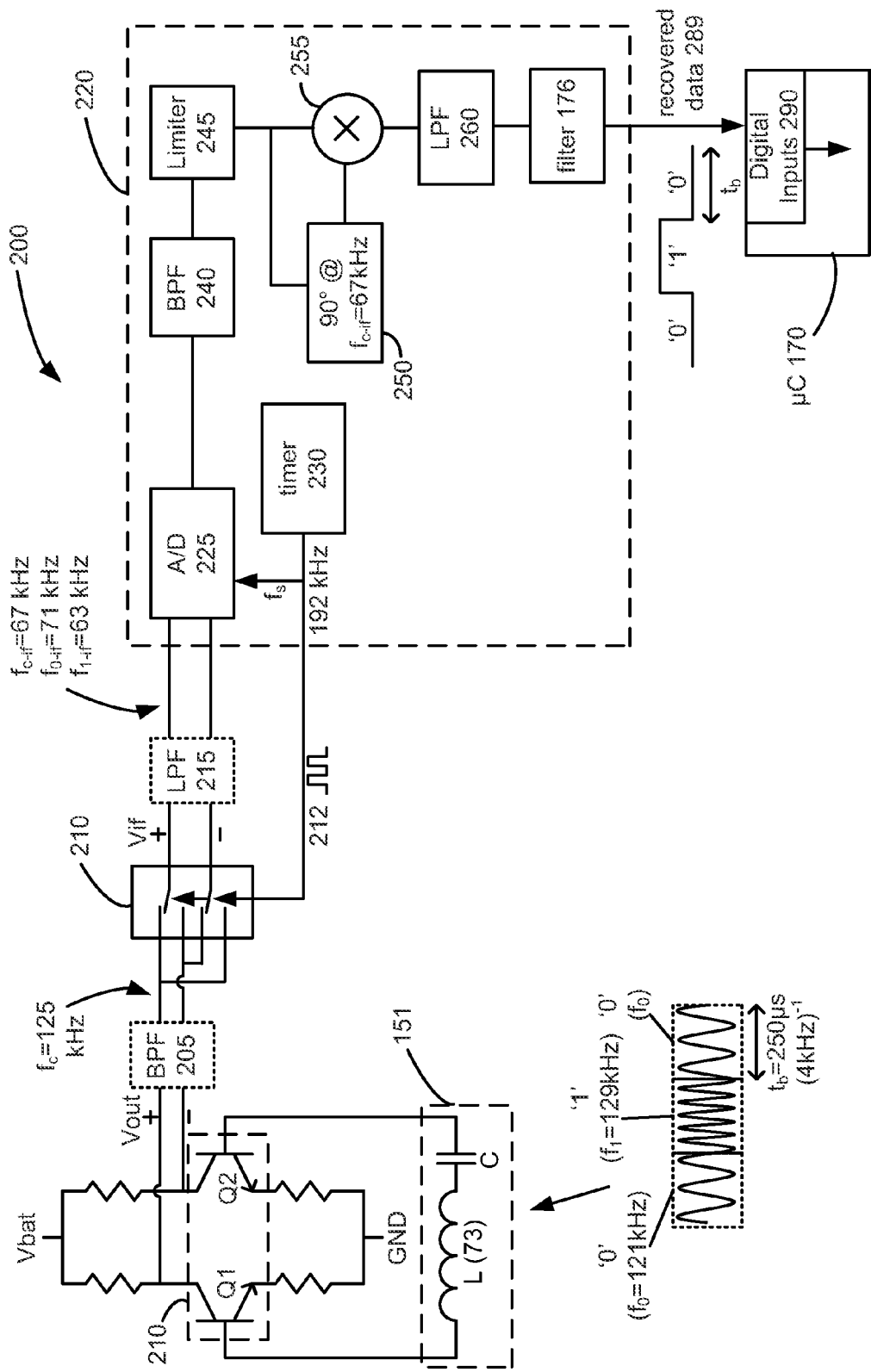
FIGS. 5 and 6 show an alternative embodiment of improved receiver and demodulation circuitry useable in an external controller in accordance with an embodiment of the invention.

Alternatively, as shown in FIG. 5, the filtering function (176) performed by the microcontroller 170 in the prior art (FIG. 3) can be moved into the DPS 220. This allows the DSP 220 to directly output digital recovered data 289 to the digital inputs 290 of the microcontroller 170.

One skilled in the art will realize that while processing in the DSP 220 is shown in FIGS. 4 and 5 as serially-connected blocks for ease of understanding, the realities of digital processing may mean that processing may not necessarily occur in the DPS 220 in such a serial fashion. Indeed, programming the DSP 220 to perform the various processes specified by the various blocks can occur in different manners, as one skilled in the art of digital processing will understand. As one skilled in the art will understand how to program a DSP to perform the various functions described, such details are omitted. The DSP 220 can boot from a serial EEPROM or from the microcontroller 170 at wake up.

Figure 6:
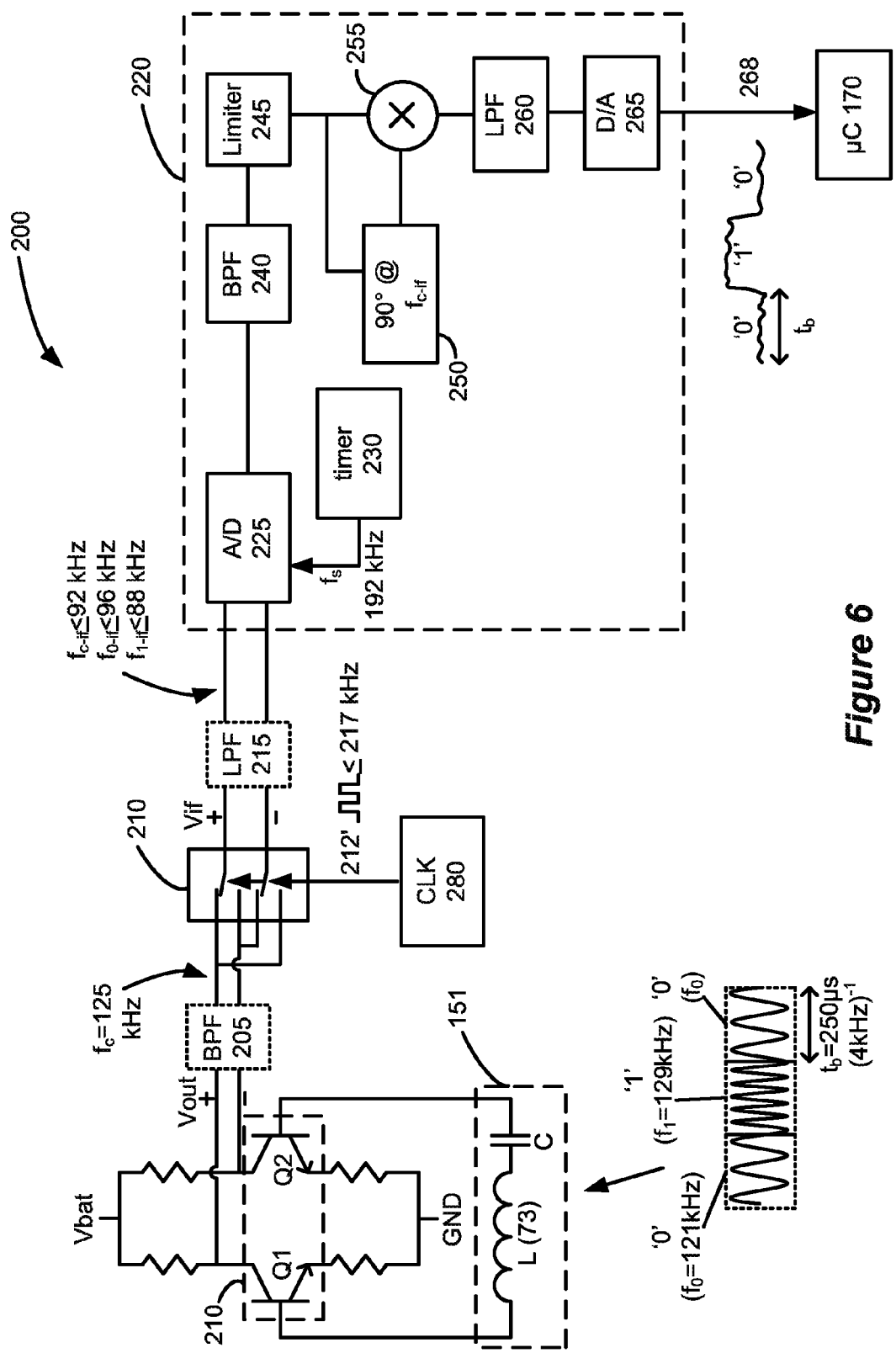

While it is preferred to use the same clock signal 212 to both sample the analog data at A/D block 225 and to control the switching circuit 210, this is not strictly necessary. It is also not necessary that the switching circuit 210 be controlled by a clock signal issued from the DSP 220, FIG. 6 shows an alternative arrangement, in which a clock generator 280 independent from the DSP 220 is used to issue a clock signal 212' to the switching circuit 210. Clock generator 280 can comprise any number of circuits used in the art to generate clock signals of set or programmable frequencies.

In the illustrated example, the frequency of the clock signal 212' is set in accordance with the sampling frequency $f_s$ used by the DSP 220 to sample the data (i.e., 192 kHz) and in accordance with the FSK frequencies of interest. Because the lowest received FSK frequency of interest comprises $f_0$=121 kHz, the frequency of clock signal 212' is set to 217 kHz or less to ensure that $f_{0-if}$ and $f_{1-if}$ can both be adequately sampled at the DSP 220 in accordance with the Nyquist sampling criteria: with clock signal 212' set to 217 kHz or less, multiplication at the switching circuit 210 yields lower intermediate frequencies of $f_{0-if}$=96 kHz or less (217 kHz or less minus 121 kHz) and $f_{1-if}$=88 kHz or less (217 kHz or less minus 129 kHz). Because the highest of these frequencies (96 kHz or less) is equal to or less than one-half of the sampling rate $f_s$=192 kHz used in the DSP 220, the Nyquist sampling criteria is met, and both FSK data states can be reliably processed and resolved.

Additionally, clock signal 212 (or 212') need not necessarily be a digital signal, but could instead comprise a reference signal that is sinusoidal or otherwise analog, but having a particular frequency. Moreover, the switching circuit 210 could comprise other types of multipliers known in the art more generally, such as mixer 154 (FIG. 3).

Still other modifications to circuitry 200 are possible. For example, while illustrated as processing differential signals, circuitry 200 is easily modified to work with non-differential signals, with amplifier 210 issuing a single analog signal to the switching circuit 210, which produces a single analog signal for input to the A/D block 225 of the DSP 220.

"Microcontroller" as used herein should be broadly construed as including all sorts of logic circuits capable of performing the various functions describe herein, including microprocessors, digital signal processors, and the like.

While illustrated as useful for the reception and demodulation of Frequency Shift Keyed (FSK) data, the disclosed circuitry 200 can also be used for the reception of data transmitted in accordance with other protocols, such as Amplitude Shift Keyed (ASK). ASK data typically comprises a single frequency, in which different data states are indicated with different amplitudes. (In the special ASK case of On-Off Keyed data, the amplitude of one of the data states is zero). This single frequency can be shifted to a lower intermediate frequency and sampled in the same manner as illustrated for FSK data. Of course, the DSP 220 would be programmed different to demodulate ASK data, as one skilled in the art will understand.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external controller for receiving wireless data from an implantable medical device, comprising:
   an antenna configured to generate an analog AC signal in response to wireless data received from the implantable medical device, wherein the wireless data comprises at least one first frequency;
   an amplifier configured to amplify the analog AC signal;
   a switching circuit controlled by a digital reference signal of a second frequency, wherein the switching circuit is configured to invert the amplified analog AC signal when the digital reference signal changes state, thereby producing an intermediate frequency analog AC signal comprising at least one intermediate frequency; and
   an analog-to-digital (A/D) converter configured to sample the intermediate frequency analog AC signal using the digital reference signal, thereby producing digital samples.

2. The external controller of claim 1, wherein the wireless data comprises Frequency Shift Keyed data comprising two first frequencies each indicative of a data state, wherein the intermediate frequency analog AC signal comprises two intermediate frequencies indicative of each data state, wherein the intermediate frequency indicative of each data state is lower than that the first frequency indicative of that data state, and wherein the second frequency is more than two times of each of the intermediate frequencies, but not more than two times of either of the first frequencies.

3. The external controller of claim 1, wherein the wireless data comprises Amplitude Shift Keyed data comprising one first frequency.

4. The external controller of claim 1, wherein the antenna comprises an L-C tank circuit.

5. The external controller of claim 1, wherein the amplifier comprises a differential amplifier.

6. The external controller of claim 5, wherein the analog AC signal, the amplified analog AC signal, and the intermediate frequency analog AC signal comprise differential signals.

7. The external controller of claim 1, wherein the at least one intermediate frequency comprises the second frequency minus the at least one first frequency.

8. The external controller of claim 1, wherein the at least one intermediate frequency is lower than the at least one first frequency, wherein the second frequency is more than two times the at least one intermediate frequency, but not more than two times the at least one first frequency.

9. The external controller of claim 1, wherein the digital reference signal comprises a single clock signal.

10. The external controller of claim 1, further comprising demodulation circuitry configured to process the digital samples to recover data states in the wireless data.

11. The external controller of claim 10, wherein the demodulation circuitry comprises a digital signal processor configured to demodulate the digital samples to recover the data states.

12. The external controller of claim 11, further comprising a microcontroller configured to receive the recovered data states.

13. The external controller of claim 10, wherein the demodulation circuitry comprises a digital signal processor configured to demodulate the digital samples, and a microcontroller configured to receive the demodulated digital samples and recover the data states.

14. An external controller for receiving wireless data from an implantable medical device, comprising:
an antenna configured to generate an analog AC signal in response to wireless data received from the implantable medical device, wherein the wireless data comprises at least one first frequency;
an amplifier configured to amplify the analog AC signal;
a multiplier configured to multiply the amplified analog AC signal with a reference signal of a second frequency, thereby producing an intermediate frequency analog AC signal comprising at least one intermediate frequency; and
an analog-to-digital (A/D) converter configured to sample the intermediate frequency analog AC signal using the reference signal, thereby producing digital samples.

15. The external controller of claim 14, wherein the wireless data comprises Frequency Shift Keyed data comprising two first frequencies, wherein each of the two first frequencies represents a data state of the wireless data.

16. The external controller of claim 14, wherein the antenna comprises an L-C tank circuit.

17. The external controller of claim 14, wherein the amplifier comprises a differential amplifier.

18. The external controller of claim 17, wherein the analog AC signal, the amplified analog AC signal, and the intermediate frequency analog AC signal comprise differential signals.

19. The external controller of claim 14, wherein the multiplier comprises a switching circuit.

20. The external controller of claim 19, wherein the switching circuit produces the intermediate frequency analog AC signal by inverting the amplified analog AC signal in accordance with the second frequency.

21. The external controller of claim 14, wherein the wireless data comprises Amplitude Shift Keyed data comprising one first frequency.

22. The external controller of claim 14, wherein the reference signal comprises a single clock signal.

23. The external controller of claim 14, further comprising demodulation circuitry configured to process the digital samples to recover the data states.

24. The external controller of claim 23, wherein the demodulation circuitry comprises a digital signal processor configured to demodulate the digital samples to recover the data states.

25. The external controller of claim 24, further comprising a microcontroller configured to receive the recovered data states.

26. The external controller of claim 23, wherein the demodulation circuitry comprises a digital signal processor configured to demodulate the digital samples, and a microcontroller configured to receive the demodulated digital samples and recover the data states.

27. The external controller of claim 14, wherein the at least one intermediate frequency equals the second frequency minus the at least one first frequency.

28. The external controller of claim 14, wherein the at least one intermediate frequency is lower than the at least one first frequency, wherein the second frequency is more than two times the at least one intermediate frequency, but not more than two times the at least one first frequency.

29. An external controller for receiving wireless data from an implantable medical device, comprising:
an antenna configured to generate an analog AC signal in response to wireless data received from the implantable medical device, wherein the wireless data comprises first frequencies each indicative of a data state;
an amplifier configured to amplify the analog AC signal;
a multiplier configured to multiply the amplified analog AC signal with a clock signal having a second frequency, thereby producing an intermediate frequency analog AC signal, wherein the intermediate frequency analog AC signal comprises intermediate frequencies each indicative of one of the data states; and
an integrated circuit, comprising:
a timer configured to issue the clock signal,
an analog-to-digital (A/D) converter configured to sample the intermediate frequency analog AC signal using the clock signal, thereby producing digital samples, and
demodulation circuitry configured to demodulate the digital samples.

30. The external controller of claim 29, wherein the wireless data comprises Frequency Shift Keyed data.

31. The external controller of claim 29, wherein the wireless data comprises Amplitude Shift Keyed data.

32. The external controller of claim 29, wherein the antenna comprises an L-C tank circuit.

33. The external controller of claim 29, wherein the multiplier comprises a switching circuit.

34. The external controller of claim 33, wherein the switching circuit inverts the amplified analog AC signal in accordance with the second frequency.

35. The external controller of claim 29, wherein the integrated circuit is configured to process the demodulated digital samples to recover data states in the wireless data.

36. The external controller of claim 35, further comprising a microcontroller configured to receive the recovered data states.

37. The external controller of claim 29, further comprising a microcontroller configured to receive the demodulated digital samples and recover data states in the wireless data.

38. The external controller of claim 29, wherein the integrated circuit comprises a digital signal processor.

39. The external controller of claim 29, wherein the intermediate frequencies equal the second frequency minus the first frequencies each indicative of data states comprising the wireless data.

* * * * *